(12) United States Patent  
Pynson et al.

(10) Patent No.: US 6,537,282 B1  
(45) Date of Patent: Mar. 25, 2003

(54) DEVICE FOR BENDING AN INTRAOCULAR LENS

(75) Inventors: Joël Pynson, Toulouse (FR); Florian David, Balma (FR)

(73) Assignee: Chauvin Opsia, Castanet Tolosan (FR)

( * ) Notice: Subject to any disclaimer, the term of this patent is extended or adjusted under 35 U.S.C. 154(b) by 0 days.

(21) Appl. No.: 09/700,399

(22) PCT Filed: Apr. 28, 1999

(86) PCT No.: PCT/FR99/01006

§ 371 (c)(1),  
(2), (4) Date: Nov. 14, 2000

(87) PCT Pub. No.: WO99/59504

PCT Pub. Date: Nov. 25, 1999

(30) Foreign Application Priority Data

May 15, 1998 (FR) ............................................ 98 06155

(51) Int. Cl.[7] .................................................. A61F 9/00
(52) U.S. Cl. ...................................... 606/107; 623/6.18
(58) Field of Search ........................ 606/107; 623/6.11, 623/6.18, 6.12

(56) References Cited

U.S. PATENT DOCUMENTS

| 5,139,501 | A |   | 8/1992  | Klaas            |         |
|-----------|---|---|---------|------------------|---------|
| 5,281,227 | A |   | 1/1994  | Sussman          |         |
| 5,290,293 | A |   | 3/1994  | Van Noy et al.   |         |
| 5,441,045 | A |   | 8/1995  | Federman et al.  |         |
| 5,702,400 | A |   | 12/1997 | Brown et al.     |         |
| 6,162,230 | A | * | 12/2000 | Polla et al.     | 606/107 |
| 6,336,932 | B1| * | 1/2002  | Figueroa et al.  | 606/107 |
| 6,355,046 | B2| * | 3/2002  | Kikuchi et al.   | 606/107 |

* cited by examiner

*Primary Examiner*—Kevin T. Truong  
(74) *Attorney, Agent, or Firm*—Young & Thompson

(57) ABSTRACT

A device for bending an intraocular lens with an optical part which is flexible, before the lens is implanted, includes at least one pair of bending support surfaces, which are designed to be able to be placed in contact with the optical part of the lens, in two areas of contact which are opposite according to a single diametral direction, and a part for maneuvering, which are designed such that, with a lens in place in a part for reception, according to a first method for actuation, two bending support surfaces come into contact with the optical part of the lens, for bending according to a first bending line, and, according to at least a second method for actuation, two other bending support surfaces come into contact with the optical part of the lens, for bending according to a second bending line, which is distinct from the first bending line. The lens can be bent according to one or the other of the bending lines.

19 Claims, 11 Drawing Sheets

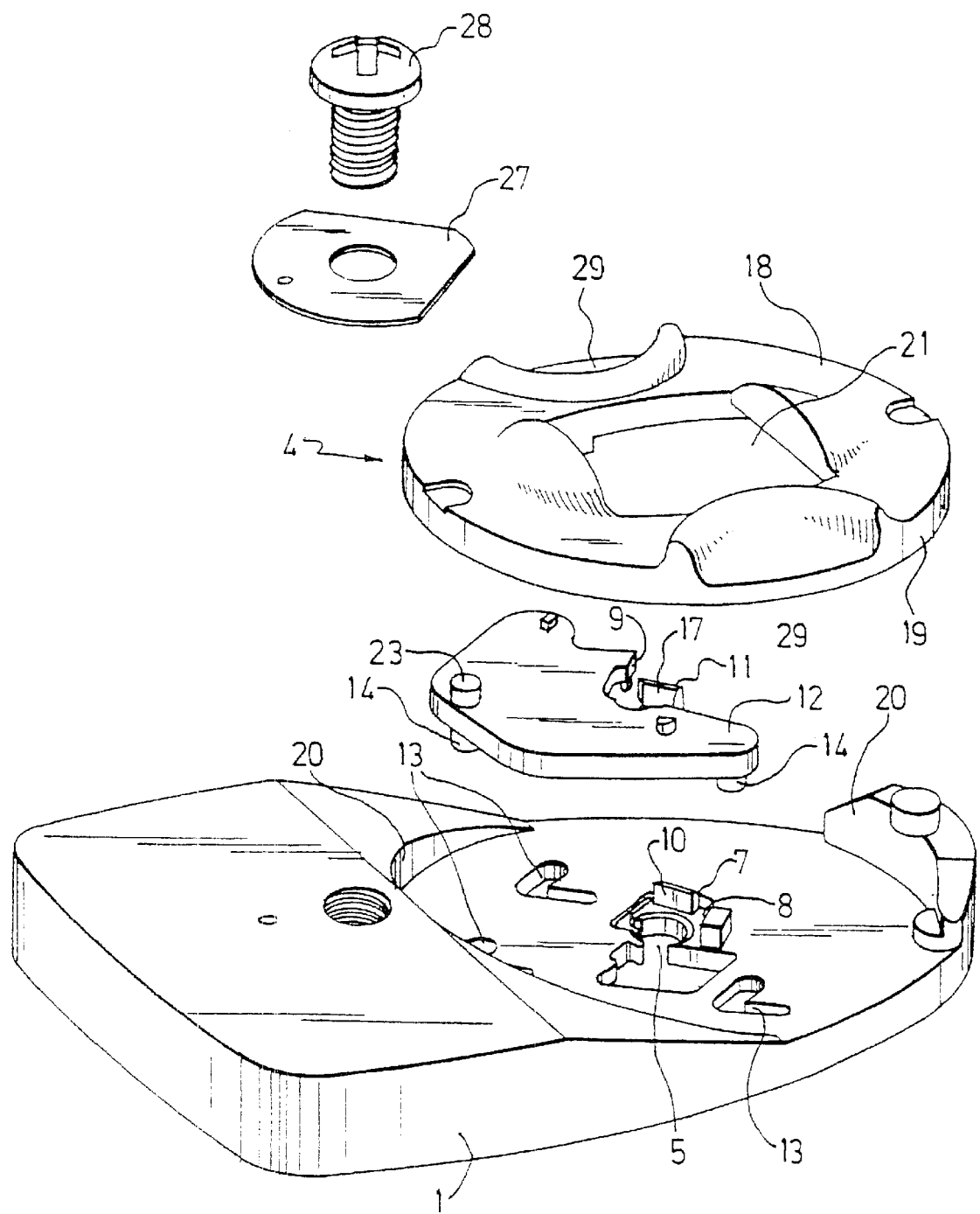

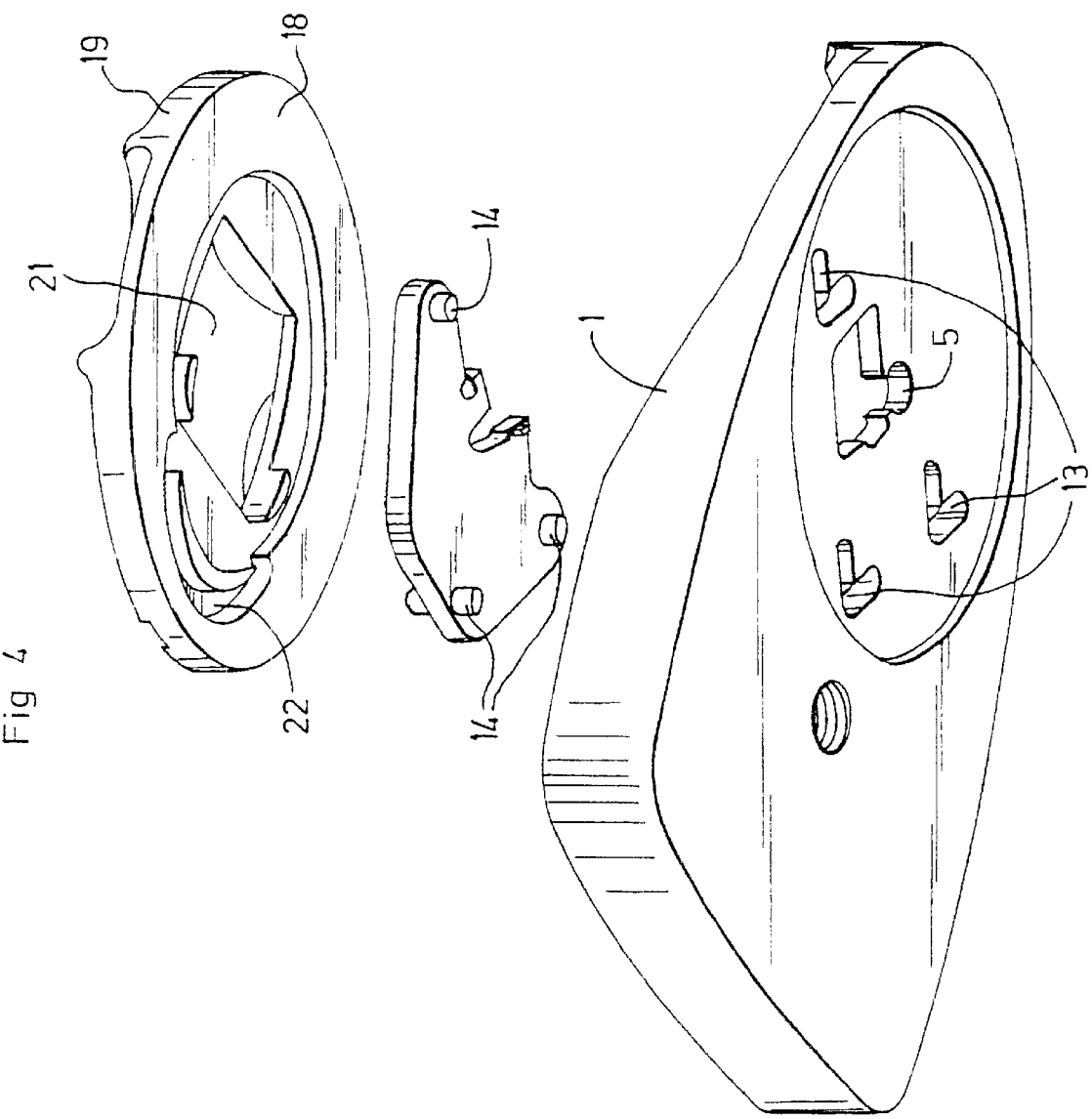

DEVICE FOR BENDING AN INTRAOCULAR LENS

BACKGROUND OF THE INVENTION

The invention relates to a device for bending an intraocular lens with a flexible optical part, before the lens is implanted in the bent condition, by being passed through a small-sized incision (conventionally of 3 to 4 mm) provided in the eye (in general in the cornea).

DESCRIPTION OF THE RELATED ART

Intraocular lenses with a flexible optical part have the advantage that they can be bent before they are introduced into the eye, which allows them to be passed into a small-sized incision. After it has been put into place in the eye, the optical part is opened out, and resumes its initial shape.

Intraocular lenses which can be bent have an optical part made of flexible material, which in particular can be selected from amongst the elastomers of polyurethane, the elastomers of silicon, and synthetic or organic gels (hydrogel, hydrated PMMA and/or HEMA, etc.).

Intraocular lenses additionally comprise a haptic part for securing to the inner wall of the eye, which can be formed from the same material as the optical part, or on the other hand can be formed from haptic loops made from another material, for example PMMA, added to the optical part.

Some intraocular lenses with a flexible optical part can be bent, at the choice of the surgeon, according to one or the other of several different bending lines, which are selected in particular according to the shape of the lens, its location or method for implantation, or the habits of the surgeon.

Thus, intraocular lenses comprising two curved haptic loops which are in the shape of a so-called "C" can be bent as a whole according to one or the other of two methods for bending.

According to the first method for bending, known as 6 o'clock-12 o'clock, the optical part is bent according to a diametral bending line, the extensions of which beyond the optical part intersect the free end part of each haptic loop.

When the lens has been bent, its two haptic loops extend longitudinally opposite one another, on the bent optical part. The implantation is then carried out in two steps. In a first step, the surgeon, who is holding grippers, between the jaws of which the bent optical part is gripped, introduces the first haptic loop, then the optical part, into the eye (into the capsule for a cataract operation), then opens the grippers in order to release the optical part. In a second step, the surgeon grips in the grippers the second haptic loop, which is still extending through the incision, and introduces it into the eye.

This first method for bending has the advantage that it is relatively easy to execute. However, it requires two implantation steps, and two passages of the grippers through the incision. The operation is thus relatively lengthy, and these repeated passages through the incision are a risk factor for the patient.

According to the second method for bending, which is known as 3 o'clock-9 o'clock, the optical part is bent along a diametral bending line, the extensions of which beyond the optical part do not intersect the haptic loops. When the lens has been bent, its two haptic loops overlap and intersect, on the same side of the bent optical part. The implantation can then be carried out in a single step, by introducing through the incision firstly the free ends of the two haptic loops, then, after rotation, the optical part.

According to this second method for bending, the operation of implantation is faster, but far more delicate, since the surgeon must control satisfactory passage and correct positioning of the lens in the incision, and opening out of the optical part, in the eye. In addition, it may happen that the haptic loops, which are presented in the incision with their free end facing forwards, collide with an ocular wall, which can give rise to lesions of the eye, or even breakage of a haptic loop.

Consequently, neither method for bending is preferable to the other, and in fact the inventors have found that, for the same intraocular lens, there are some surgeons who recommend and use the first method for bending, i.e. 6 o'clock-12 o'clock, and others who recommend and use the second method for bending, i.e. 3 o'clock-9 o'clock. In addition, it has been found that the method for bending selected can vary according to the personality of the surgeon, i.e. according to his tastes or habits, but also, for the same surgeon, according to the cases of surgical operations to be carried out, such that it is not possible to know in advance the method for bending which the surgeon will select for an operation.

U.S. Pat. No. 5,290,293 describes bending grippers in a single piece, which comprise receptacles to accommodate the implant, and a pair of bending support surfaces, which approach one another substantially in translation, according to a diametral direction of the lens, when manoeuvring handles are actuated, which are connected to one another by a flexible portion which forms a hinge. By means of this device, when the intraocular lens has been placed in the accommodation receptacles, it can be bent only according to a single bending line, perpendicular to the said diametral direction, only according to the 6 o'clock-12 o'clock bending method. In addition, the lens must firstly be handled in order to be put into place in the accommodation receptacles of the gripper, in order to be bent.

U.S. Pat. No. 5,139,501 describes a device for bending comprising a bending support surface which is secured onto a frame, and a bending support surface which is formed at the end of a slide, which is fitted such as to be mobile in translation relative to the frame, with studs for attachment of the haptic loops. This device permits bending only according to the 3 o'clock-9 o'clock method for bending. In addition, it should be noted that the slide is guided in translation towards the lens in a dovetail slide, such that any wear dust resulting from the friction of the parts during this displacement tends to be carried towards the lens, with the risk of dirtying the latter before the implantation takes place.

These devices for bending are only slightly successful commercially. In fact, when they are provided together with the lens (for example as packaging for the lens, which is placed in the device in the factory), the surgeon can use the lens only with the method for bending of the corresponding device for bending. It is therefore necessary either to plan to select the method for bending before the purchase is made, which is rarely possible, or to constitute stocks with each type of device for bending. In addition, if the device for bending is provided independently from the lens, risky handling is necessary in order to place the lens in the device for bending, which increases the time necessary for the operation, and the risks of dirtying and deterioration of the lens.

U.S. Pat. No. 5,281,227 describes a device for bending a flexible lens comprising a frame, a one-way bending unit comprising a pair of bending jaws supported by resilient flexible side members of this bending unit, which is fitted such as to rotate on the frame, and can be disconnected from the frame, and a cap. In order to bend the lens in place between the jaws of the bending unit, the cap is removed, then the bending unit is placed according to the required orientation, by being pivoted relative to the frame, the frame preventing the lens from pivoting on its support, then the bending unit is disconnected from the frame, the lens remaining in place between the jaws of the bending unit, then a gripper to grasp the lens is inserted between the jaws of the bending unit, and the two jaws are drawn close to one another by resilient deformation of the side members. This device has the disadvantage in particular that it requires sliding of the lens support of the bending unit relative to the lens, during pivoting for orientation of the bending unit, with the risk of damaging the condition of the surface of the optical part of the lens, which is particularly sensitive. In addition, bending of the lens requires a large number of handling operations, some of which are relatively delicate, by the surgeon. Furthermore, if there is any difficulty during the bending, there is a risk that the lens will fall on the floor, and be lost definitively. Moreover, the surgeon cannot leave the bending unit in an intermediate bending position, owing to the resilience of the side members. Also, the action of the surgeon on the side members is implemented directly, without any gearing down, on the bending jaws and on the lens, such that the bending cannot be carried out gradually and accurately. The quality of the bending is therefore closely associated with the skill of the surgeon.

SUMMARY OF THE INVENTION

The object of the invention is thus to eliminate these disadvantages, by providing a device for bending an intraocular lens, which, without prior handling of the lens relative to the device, makes it possible to bend the lens according to one or another of several methods for bending, corresponding to distinct diametral bending lines, at the choice of the surgeon, immediately before the operation of implantation.

The object of the invention is thus in particular to provide a device for bending which makes it possible to carry out bending of an intraocular lens with haptic loops in the shape of a "C", at the choice of the surgeon, immediately before the operation of implantation, without prior handling of the lens relative to the device, i.e. according to a 6 o'clock-12 o'clock bending method, or according to a 3 o'clock-9 o'clock bending method.

The object of the invention is also to provide a device for bending of this type, which is simple and inexpensive.

More particularly, the object of the invention is to provide methods for production of a device for bending of this type, consisting of a minimal number of separate parts, and in particular at the most four parts which are mobile relative to one another.

The object of the invention is also, and more particularly, to provide methods for production of a device for bending of this type, which have limited risks of dirtying and deterioration of the lens during bending.

The object of the invention is also, and more particularly, to provide methods for production of a device for bending of this type, which are simple and immediately understandable, and which in particular make it possible to select the method for bending easily, quickly, and without risk of error.

The object of the invention is also, and more particularly, to provide methods for production of a device for bending of this type, which is quick and easy to handle, and by means of which the bending can be executed gradually, slowly and accurately, without requiring particular skill by the surgeon. For this purpose, the object of the invention is more particularly to provide methods for production of a device for bending of this type, in which the movement imparted by the surgeon on each mobile manoeuvring unit is geared down, the path of displacement of the corresponding mobile bending support surface being reduced relative to that of the mobile manoeuvring unit.

The object of the invention is also, and more particularly, to provide methods for production of a device for bending of this type, in which the device can act as packaging for the intraocular lens, and can be sterilised.

For this purpose, the invention relates to a device for bending an intraocular lens with a flexible optical part, before the lens is implanted, comprising:
  means for reception of the lens;
  at least one pair of bending support surfaces, which are designed to be able to be placed in contact with the optical part of the lens, in two areas of contact which are opposite according to a single diametral direction;
  means for manoeuvring, which are connected to at least one bending support surface, and, when they are actuated, are designed to control displacement towards another bending support surface of a single pair of bending support surfaces, characterised in that the means for manoeuvring are designed such that, with a lens in place in the means for reception:
  according to a first method for actuation of the means for manoeuvring, two bending support surfaces come into contact with the optical part of the lens, in two areas of contact which are opposite according to a first diametral direction, for bending according to a first bending line;
  according to at least a second method for actuation of the means for manoeuvring, two bending support surfaces come into contact with the optical part of the lens, in two areas of contact which are opposite according to a second diametral direction, which is different from the first diametral direction, for bending according to a second bending line, which is distinct from the first bending line, such that the lens can be bent according to one or the other of the different bending lines.

Advantageously and according to the invention, in particular when the intraocular lens is of the type comprising two haptic loops in the shape of a "C" (throughout the text, this expression denotes curved haptic loops which are deformable flexurally, which are connected to the periphery of the optical part by one of their ends, and have another, free end, the two loops having a shape which is globally symmetrical relative to one another, in relation to the optical axis of the optical part), the first diametral direction and the second diametral direction forming between one another an angle of between 60° and 120°, such that the lens can be bent according to one or the other of two bending lines which form between one another an angle of between 60° and 120°.

In a variant, advantageously and according to the invention, the device for bending comprises:
  a frame which includes the means for reception of the lens;
  at least one pair of bending support surfaces, which are designed to be able to be placed radially in contact with the periphery of the optical part of the lens, in two diametrically opposite areas of contact, at least one of the two bending support surfaces, known as the mobile bending support surface of a pair of bending support surfaces, being fitted relative to the frame such that it can be drawn closer to the other bending support surface of this pair of bending support surfaces, and in that the means for manoeuvring comprise at least one mobile manoeuvring unit, which is connected to at least one mobile bending support surface, in order to control the displacements of the latter relative to the means for reception, when this mobile manoeuvring unit is actuated.

According to an advantageous characteristic of the invention, the device for bending is characterised in that it comprises:

- a first pair of bending support surfaces, which are designed to be able to be placed in contact with the periphery of the optical part of the lens, in two opposite areas of contact, according to the first diametral direction, and, under the effect of the actuation of at least one mobile manoeuvring unit according to the first embodiment of actuation, to produce bending of the lens according to the first line of bending;
- at least one second pair of bending support surfaces, distinct from the first pair of bending support surfaces, the bending support surfaces of this second pair being designed to be able to be placed in contact with the periphery of the optical part of the lens, in two opposite areas of contact, according to the second diametral direction, and, under the effect of the actuation of at least one mobile manoeuvring unit according to the second embodiment of actuation, to produce bending of the lens according to the second line of bending, which is distinct from the first line of bending.

In one embodiment, and according to the invention, the device for bending is characterised in that the means for manoeuvring comprise at least two mobile manoeuvring units, one of which is connected to at least one first mobile bending support surface of a first pair of bending support surfaces, and the other of which is connected to at least one second mobile bending support surface of a second pair of bending support surfaces.

According to another embodiment, advantageously and according to the invention, the device for bending is characterised in that the means for manoeuvring comprise a mobile manoeuvring unit, which is connected to at least one first mobile bending support surface of the first pair of bending support surfaces, and to at least one second mobile bending support surface of the second pair of bending support surfaces, this mobile manoeuvring unit being designed to be able to be actuated either according to the first method for actuation, or according to the second method for actuation.

Advantageously and according to the invention, the device for bending is characterised in that the mobile manoeuvring unit is fitted such as to rotate relative to the frame, in that the first method for actuation corresponds to displacement in rotation of the mobile manoeuvring unit in a first direction of rotation, and in that the second method for actuation corresponds to displacement in rotation of the mobile manoeuvring unit in the second direction of rotation, opposite to the first direction of rotation. As a variant or in association, the device for bending is characterised in that the mobile manoeuvring unit is fitted relative to the frame such that it can be displaced according to at least two distinct directions of translation, one of which corresponds to the first method for actuation, whereas the other corresponds to the second method for actuation. According to another variant, or in association, the device for bending is characterised in that the mobile manoeuvring unit is fitted relative to the frame such that it can be displaced according to at least one direction of translation, and according to at least two opposite directions according to this direction of translation, one of which corresponds to the first method for actuation, whereas the other corresponds to the second method for actuation.

It should be noted that there is nothing to prevent the mobile manoeuvring unit from being fitted such as to rotate and slide, i.e. with displacement components which are combined in rotation and in translation.

In addition, advantageously and according to the invention, the device for bending is characterised in that a first mobile bending support surface of the first pair of bending support surfaces and a second mobile bending support surface of the second pair of bending support surfaces are integral with a single intermediate mobile part, which is fitted and guided relative to the frame, and is connected to the mobile manoeuvring unit, such as to be able to be entrained in displacement under the effect of actuation of this mobile manoeuvring unit according to one or the other of the methods for actuation.

Also, in the different embodiments, advantageously and according to the invention, a mobile manoeuvring unit is connected to each mobile bending support surface of which it controls the displacements, by means of a cam and contact slide system. Thus, the movement of actuation by the practitioner on this mobile manoeuvring unit can have a path which is longer than that of the displacement of the mobile bending support surface.

In addition, in some embodiments, advantageously and according to the invention, each pair of bending support surfaces comprises a bending support surface which is fixed relative to the frame. Also, in some embodiments, advantageously and according to the invention, each mobile bending support surface is fitted relative to the frame such as to be able to be mobile at least substantially in translation, in particular according to a corresponding diametral direction.

In addition, advantageously and according to the invention, the device for bending is characterised in that the means for reception are designed to receive the intraocular lens, which is oriented, in particular relative to the frame, according to a single possible direction. In particular, and according to the invention, the means for reception advantageously comprise receptacles to accommodate the haptic part of the lens, and in particular haptic lenses in the shape of a "C". The means for reception can be formed entirely or partially by the (fixed or mobile) bending support surfaces themselves.

It should be noted that since the lens is in place in the means for reception, according to its predetermined orientation, the surgeon does not need to handle the lens with grippers or the like, in order to select the method for bending. In fact, it is sufficient for him to actuate the means for manoeuvring of the device for bending, according to the method for actuation appropriate for the bending selected.

In addition, advantageously and according to the invention, the device for bending is characterised in that it constitutes packaging for an intraocular lens, and includes a cap which is closed onto the lens which is in place in the means for reception, this cap being designed to be able to be opened in order to permit access to the lens. Advantageously and according to the invention, this cap is designed also to serve the purpose of keeping the lens in place in the means for reception, perpendicularly to the plane of the optical part, i.e. according to the optical axis.

In addition, advantageously and according to the invention, the cap is designed such that, in the position in which it is closed onto the lens, it prevents any premature displacement of the means for manoeuvring, and, in its open position, it permits actuation of the means for manoeuvring according to one or the other of the methods for actuation.

The invention also extends to a device for bending, which is characterised in combination by some or all of the characteristics described previously or hereinafter.

BRIEF DESCRIPTION OF THE DRAWINGS

Other objects, characteristics and advantages of the invention will become apparent from reading the following description, provided with reference to the attached figures, in which:

FIGS. 3 and 4 are exploded schematic perspective views respectively from three-quarters above, and three-quarters below, of a device for bending according to a second embodiment, which is similar to the first embodiment of the invention, but is made of metal and does not have a cap;

FIGS. 6, 7a and 8 are schematic perspective views, illustrating respectively three other embodiments of a device for bending according to the invention, FIG. 7b being a schematic plan view on a smaller scale, of the frame of the device in FIG. 7a;

In the different figures, the same references are used to designate the same functional elements.

DESCRIPTION OF THE PREFERRED EMBODIMENTS

Figure 1:
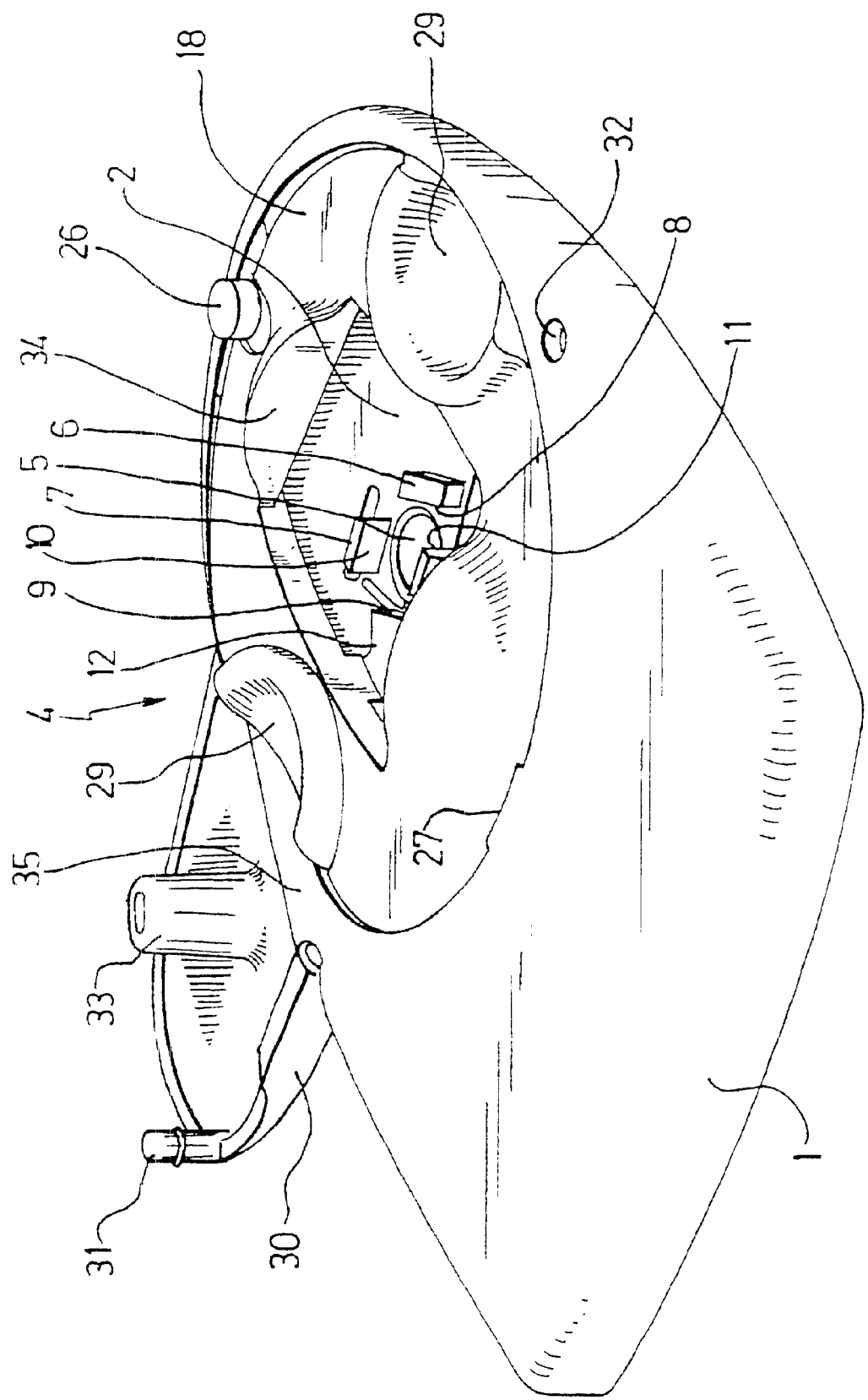
FIGS. 1 and 2 are schematic perspective views of a device for bending according to a first embodiment of the invention, made of synthetic materials, illustrated respectively with the cap open and the cap closed.
Figure 2:
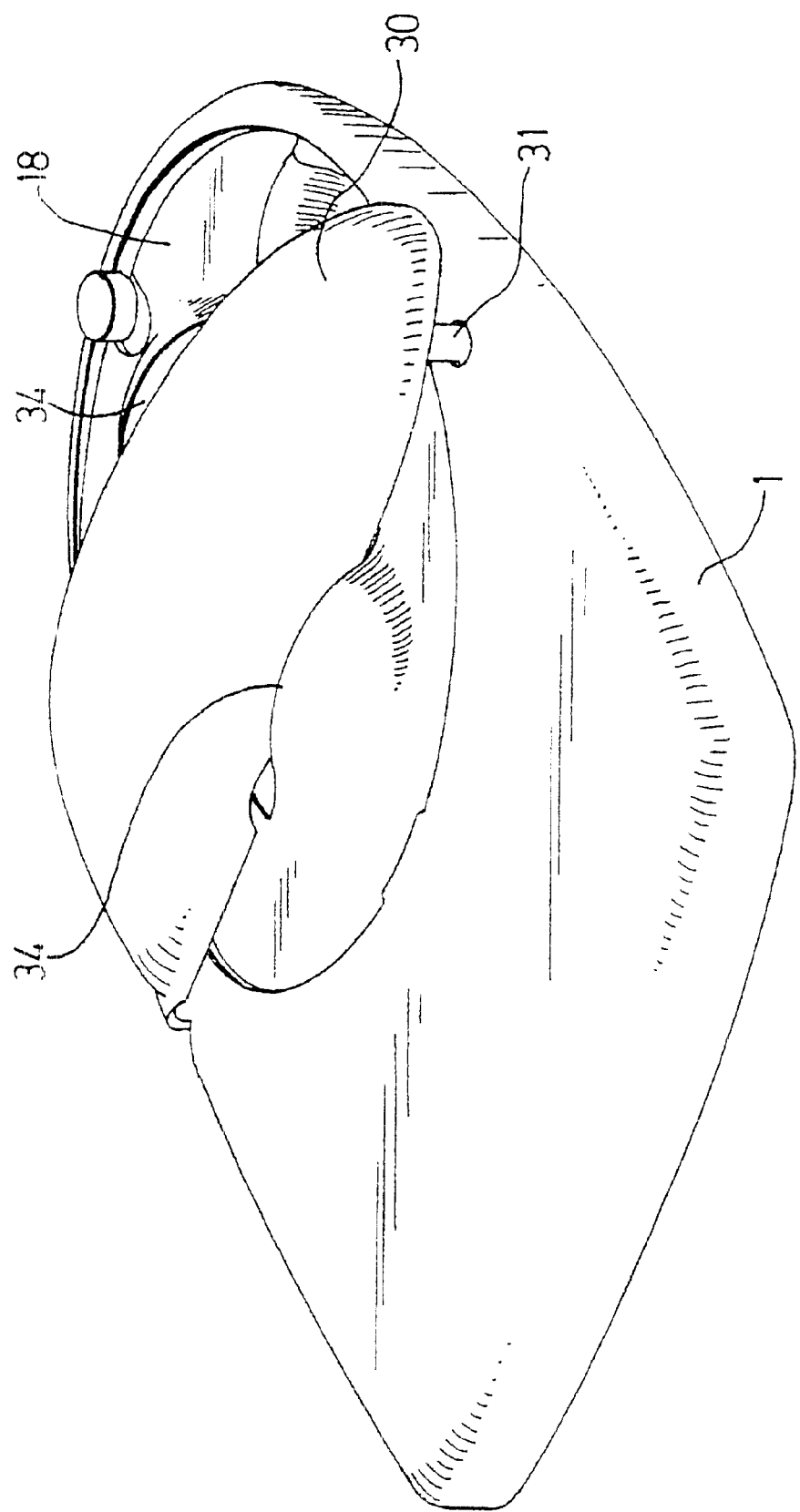

The first embodiment in FIGS. 1 and 2, and the second embodiment in FIGS. 3 and 4 have the same functional elements, and the same kinematic system, from the point of view of bending of the intraocular lens. They differ only in the material used (synthetic material in FIGS. 1 and 2, metal such as aluminium in FIGS. 3 and 4), and in that the first embodiment is provided with an articulated cap 30, and can act as packaging for the intraocular lens 3.

In these figures, the device for bending comprises a frame 1, which defines a base 2 to receive an intraocular lens 3 to be bent, in order to be implanted in the eye of a patient. The frame 1 is flat as a whole, and has shapes and dimensions which are preferably designed to allow it to be grasped in one hand, the other hand being used to actuate the means 4 for manoeuvring fitted onto the frame 1 for bending of the intraocular lens 3. In the present description, the frame 1 and the base 2 are assumed to extend horizontally. The intraocular lens 3 comprises an optical part 3a made of flexible material, and two haptic loops 3b in the shape of a "C".

The base 2 for reception is advantageously provided with a cylindrical central recess or aperture 5 with a vertical axis, opposite the optical part 3a, with a diameter smaller than that of the optical part 3a, in order to facilitate bending and minimise the friction of the peripheral edges of the optical part 3a on the base 2 during bending. The diameter of the central recess or aperture 5 is for example approximately 4 mm.

The base 2 supports two fixed studs 6, 7, which are disposed at least substantially at 90° relative to one another, around and in the vicinity of the central recess or aperture 5. Each of these studs 6, 7 has a surface, respectively 8 and 10, which extends upwards from the base 2, and at least substantially perpendicularly to the radial direction of the central recess or aperture 5 and of the optical part 3a of a lens in place on the base 2. These surfaces 8, 10 define two fixed bending support surfaces 8, 10, which are designed to come into contact with the periphery of the optical part 30.

The device comprises an intermediate mobile part 12, which is fitted and guided on the frame 1 by means of at least one groove 13 in the shape of a "V", in the base 2, which receives at least one lug 14 of the intermediate mobile part 12, in particular by means of a series of grooves 13 and lugs 14. As can be seen in FIGS. 3 and 4, the base 2 comprises three grooves 13 in the shape of a "V", each of which has two branches, i.e. a first branch and a second branch, which form between one another an angle which is at least substantially equivalent to the angle formed between the two potential bending lines required for the lens 3. The various grooves 13 (i.e. their corresponding branches) are parallel to one another. The intermediate mobile part 12 comprises three lugs 14, which project downwards, such that they can slide in the three grooves 13. The intermediate mobile part 12 can thus be displaced in translation relative to the base 2, according to one or the other of the directions which correspond to the directions of the two branches of the grooves 13.

The intermediate mobile part 12 has two surfaces, respectively 9 and 11, which extend upwards relative to the base 2. When the intermediate mobile part 12 is in the initial position before being bent, the lugs 14 being placed at the top of the grooves 13 in the shape of a "V", these surfaces 9, 11 extend at least substantially perpendicularly to the radial direction of the central recess or aperture 5, and of the optical part 3a of a lens in place on the base 2.

Each of these surfaces 9, 11, which is displaced together with the intermediate mobile part 12, defines a mobile bending support surface 9, 11, which is designed to come into contact with the periphery of the optical part 3a of the lens.

The device for bending thus comprises two pairs 8, 9 and 10, 11 of bending support surfaces.

The first pair 8, 9 comprises a fixed bending support surface 8, which is integral with the base 2, and a mobile bending support surface 9 which is integral with the intermediate mobile part 12, and these two bending support surfaces 8, 9 are designed to be able to be placed in contact with the periphery of the optical part 3a of the lens 3 in place on the base 2, in two areas of contact which are opposite according to a first diametral direction 15, which is at least substantially parallel to the direction of the first branches of the grooves 13 in the shape of a "V".

The second pair 10, 11 comprises a fixed bending support surface 10, which is integral with the base 2, and a mobile bending support surface 11, which is integral with the intermediate mobile part 12, and these two bending support surfaces 10, 11 are designed to be able to be placed in contact with the periphery of the optical part 3a of the lens 3 in place on the base 2, in two areas of contact which are opposite according to a second diametral direction 16, which is at least substantially perpendicular to the first diametral direction 15, this second diametral direction 16 being at least substantially parallel to the direction of the second branches of the grooves 13 in the shape of a "V".

In the initial position, the two mobile bending support surfaces 10, 11 are disposed around the central recess or aperture 5, at least substantially at 90° relative to one another, around and in the vicinity of this central recess or aperture 5. The two bending support surfaces 8, 9 and 10, 11 of a single pair extend at least substantially parallel to one another and perpendicularly to the corresponding diametral direction 15, 16.

The intermediate mobile part 12 is designed to permit passage of a haptic loop 3b around and behind one 11 of the two mobile bending support surfaces (that of the second pair), and comprises a recess 17 for this purpose. The other haptic loop 3b of the lens 3 can be passed behind the stud 7 which defines the fixed bending support surface 10 of the second pair. The intermediate mobile part 12 and/or the other stud 6 are designed to prevent passage of the haptic loops 3b behind the other bending support surfaces 8, 9 of the first pair of bending support surfaces. Thus, the lens 3 can be placed only according to a single possible orientation relative to the base 2.

The device for bending also comprises a rotary mobile manoeuvring unit 18, which is generally in the shape of a ring, and acts as a means for manoeuvring. This mobile manoeuvring unit 18 is recessed in its central part, such as to have an access opening 21 opposite the lens 3 in place on the base 2, and has a circular outer narrow edge 19, which is slid against one or a plurality of cylindrical guide surfaces 20 which are integral with the frame 1, and are designed to receive the mobile manoeuvring unit 18 and guide it in rotation relative to the frame 1.

Figure 5A:
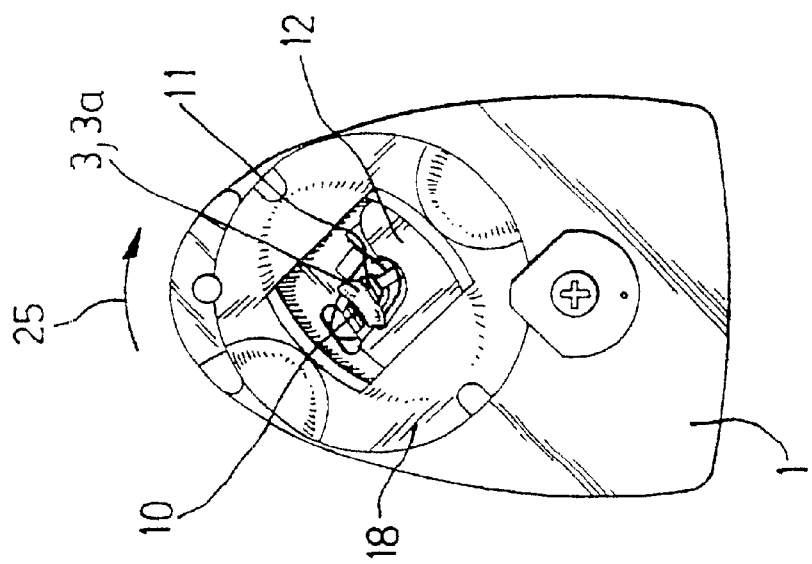
FIGS. 5a, 5b, 5c are schematic plan views illustrating the device for bending in FIGS. 3 and 4, respectively in the initial position, in the 6 o'clock-12 o'clock position for bending, and in the 3 o'clock-9 o'clock position for bending of an intraocular lens.
Figure 5B:
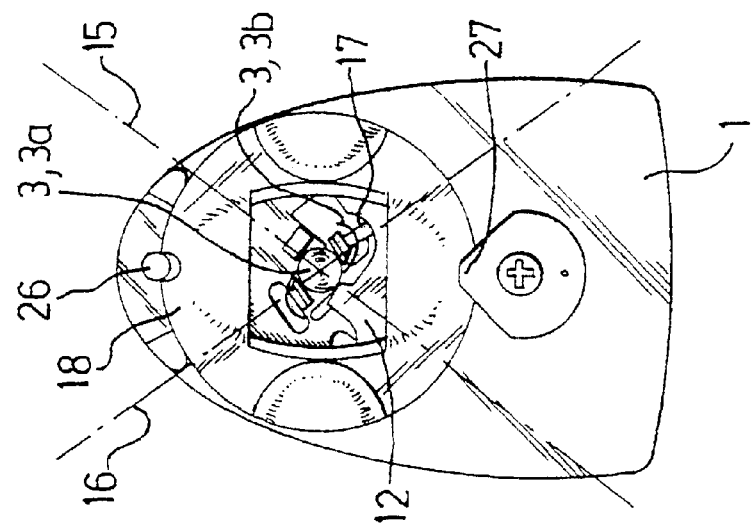
Figure 5C:
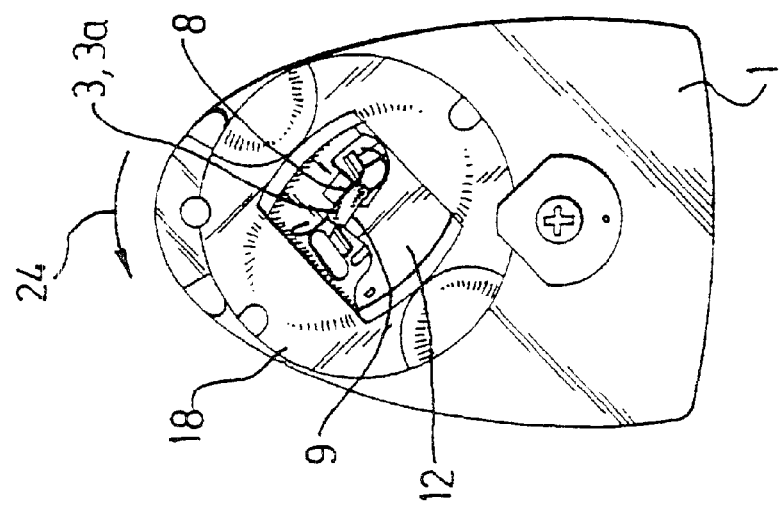

The rotary mobile manoeuvring unit 18 is connected to the mobile bending support surfaces 9, 11, i.e. to the intermediate mobile part 12, by means of a cam mechanism 22 and contact slide 23. Thus, the intermediate mobile part 12 supports a slide 23, which projects upwards in order to cooperate with a cam 22 which is provided recessed beneath the mobile manoeuvring unit 18. The shape of the cam 22 is designed such that when the mobile manoeuvring unit 18 is displaced in a first direction of rotation 24 (FIG. 5b), the intermediate mobile part 12 is displaced according to the first diametral direction 15 (the lugs 14 being guided in the first branches of the grooves 13), and when it is displaced in the second direction of rotation 25 (FIG. 5c), opposite the first direction of rotation 24, the intermediate mobile part 12 is displaced according to the second diametral direction 16 (the lugs 14 being guided in the second branches of the grooves 13).

The mobile manoeuvring unit 18 covers the intermediate mobile part 12, and the assembly is kept in place axially relative to the frame 1 by stops 26, 27.

In the embodiment in FIGS. 3 and 4, the device comprises a fixed stop 26, which projects horizontally above the edge of the upper surface of the mobile manoeuvring unit 18, and diametrically opposite this fixed stop 26, a detachable stop 27, which is secured by a screw 28, such as to permit fitting and removal of the mobile manoeuvring unit 18.

In the embodiment in FIGS. 1 and 2, the two stops 26, 27 are fixed, and the mobile manoeuvring unit is forced by resilient deformation beneath these stops 26,27 which are made of plastics material.

The mobile manoeuvring unit 18 comprises two manoeuvring cut-outs 29, which facilitate holding in the hand and actuation in rotation of the unit.

The first method for actuation (FIG. 5b) of the mobile manoeuvring unit 18 according to the first direction of rotation 24 has the effect of bringing the mobile bending support surface 9 of the first pair of bending support surfaces, radially closer to the fixed bending support surface 8 of this first pair, according to the first radial direction 15, which gives rise to bending of the optical part 3a of the lens, according to a first, 6 o'clock-12 o'lock bending line, which is at least substantially perpendicular to the first diametral direction 15.

The second method for actuation (FIG. 5c) of the mobile manoeuvring unit 18 according to the second direction of rotation 25 has the effect of bringing the mobile bending support surface 11 of the second pair of bending support surfaces, radially closer to the fixed bending support surface 10 of this second pair, according to the second radial direction 16, which gives rise to bending of the optical part 3a of the lens, according to a second, 3 o'clock-9 o'clock bending line, which is at least substantially perpendicular to the second diametral direction 16.

The cap 30 of the bending device of the first embodiment is articulated on the side of the frame 1, for example by a film hinge 35, formed by a thin strip of synthetic material. This cap comprises a lug 31 for locking in a closed position, which is forced into an aperture 32 in the frame 1, and an axial extension 33, which extends downwards in the closed position, in order to keep a lens 3 axially in place on the reception base 2. In addition, in the closed position, the cap 30 is engaged between two straight walls 34 of the mobile manoeuvring unit 18, such that it then prevents any premature displacement in rotation of this mobile manoeuvring unit 18.

When the cap is open (FIG. 1), the mobile manoeuvring unit 18 is released, and can be actuated in one direction of rotation or the other 24, 25.

In the embodiments in FIGS. 1 and 2 and 3 and 4, the device for bending according to the invention substantially consists of three parts which are mobile relative to one another, i.e. the frame 1, the intermediate mobile part 12, and the mobile manoeuvring unit 18.

Figure 6:
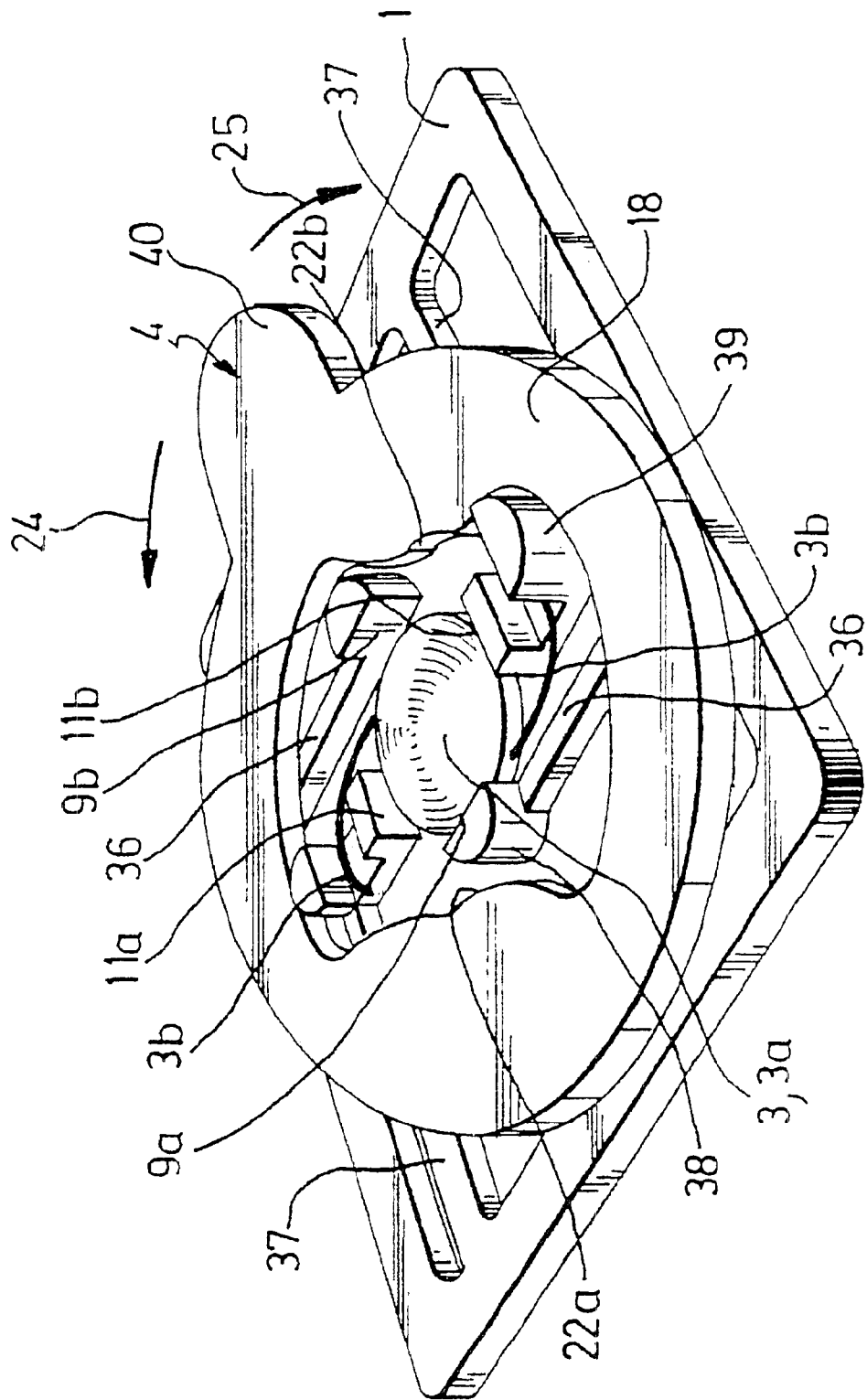

According to the embodiment shown in FIG. 6, the device for bending consists only of two parts, i.e. the frame 1 and the mobile manoeuvring unit 18 which is fitted such as to rotate on this frame 1. Each mobile bending support surface 9a, 9b, 11a, 11b is formed by an end stud of a flexible arm 36, 37, which is integral with the frame 1, and extends horizontally and perpendicularly to the diametral direction according to which the support surface must be displaced.

In addition, according to this embodiment, all the bending support surfaces are mobile. The first pair of bending support surfaces comprises two mobile bending support surfaces 9a, 9b, and the second pair of bending support surfaces comprises two mobile bending support surfaces 11a, 11b. The mobile manoeuvring unit 18 comprises two cams 22a, 22b, which delimit its central aperture 21, and are designed to be in contact simultaneously with the semi-cylindrical rear surfaces 38 or 39 of the two studs which form the two bending support surfaces 9a, 9b or 11a, 11b of a single pair of bending support surfaces. One of the cams 22a controls one 9a, 11a of the bending support surfaces, whereas the other cam 22b controls the other bending support surface 9b, 11b. The bending support surfaces 9a, 9b of the first pair have cut-outs which form receptacles to accommodate the haptic loops 3b of the lens. In the variant shown, the lens 3 is kept in place axially, i.e. it is supported by the frame 1, simply by means of these accommodation receptacles, by means of its haptic loops 3b.

Figure 7:
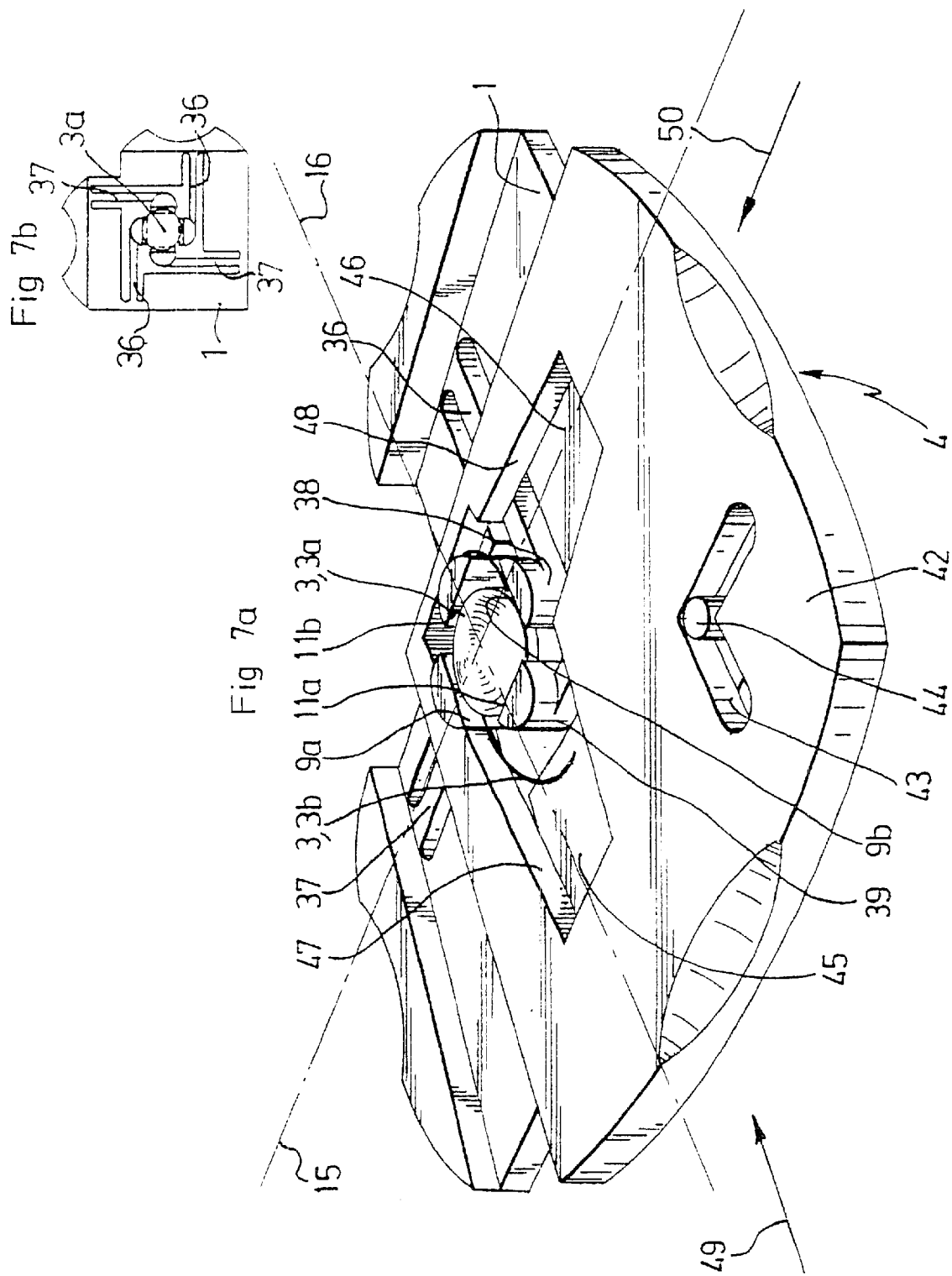

As in the case of the embodiment shown in FIG. 7b, the mobile bending support surfaces 9a, 9b, 11a, 11b can have radial extensions towards the interior, beneath the optical part 3a of the lens, such as to form at least partially means to receive the lens 3 and support it axially.

The mobile manoeuvring unit 18 comprises a tab 40 for actuation, and is guided on the frame 1 by guide means which rotate in a circular groove/circular grooves and a lug/lugs. When the mobile manoeuvring unit 18 is actuated in the first direction of rotation 24, the cams 22a, 22b come into contact with the rear surfaces 38 of the studs which form the two mobile bending support surfaces 9a, 9b of the first pair, which approach one another radially by flexure of the arms 36 which support them. This displacement by flexure can be assimilated to translation according to the first diametral direction 15, taking into account the length of the arms 36, and the short path of displacement induced. The lens 3 is then bent according to a 6 o'clock-12 o'clock bending line.

When the mobile manoeuvring unit 18 is actuated in the second direction of rotation 25, the cams 22a, 22b come into contact with the surfaces 39, and the two mobile bending support surfaces 11a, 11b approach one another radially by flexure of the arms 37 which support them, the displacement being assimilable to translation in the second diametral direction 16. The lens 3 is then bent according to a 3 o'clock-9 o'clock bending line.

In the embodiment in FIGS. 7a and 7b, the bending device comprises a mobile manoeuvring unit 42 which is not guided in rotation on the frame 1, but is guided in translation according to one or the other of the two directions 49, 50, respectively perpendicular to the first diametral direction 15 and the second diametral direction 16. For this purpose, at least one groove 43 in the shape of a "V", with two branches at 90°, is provided in the mobile manoeuvring unit 42, and a lug 44, which is integral with the frame 1 slides in the groove 43 in the shape of a The mobile manoeuvring unit 42 comprises two trapezoidal openings 45, 46 at 90° relative to one another, each of which defines a pair of straight cams 47, 48, which converge relative to one another, for the rear surfaces 38, 39 of the studs which support the mobile bending surfaces 9a, 9b, 11a, 11b.

In this case also, the frame 1 supports two pairs of mobile bending support surfaces 9a, 9b, 11a, 11b, which are formed by studs at-the end of flexible arms 36, 37 of the frame 1. Each stud also comprises a radial extension (FIG. 7b) towards the interior, beneath the optical part 3a of the lens, in order to receive the lens and support it axially. The radial length of these extensions is not too long to prevent satisfactory bending of the lens 3.

When the unit 42 is actuated according to a first direction of translation 49 relative to the frame, 1, the two cams 47 of the first opening 45 come into contact with the rear surfaces 38 of the studs which support the two mobile bending support surfaces 9a, 9b of the first pair, and bring the surfaces closer to one another radially according to the first diametral direction 15. The lens 3 is bent according to a 6 o'clock-12 o'clock bending line.

When the unit 42 is displaced according to the second direction of translation 50, the two cams 48 of the second opening 46 come into contact with the rear surfaces 39 of the studs which support the mobile bending support surfaces 11a, 11b of the second pair, and bring the surfaces closer to one another radially according to the second diametral direction 16. The lens 3 is bent according to a 3 o'clock-9 o'clock bending line.

Figure 8:
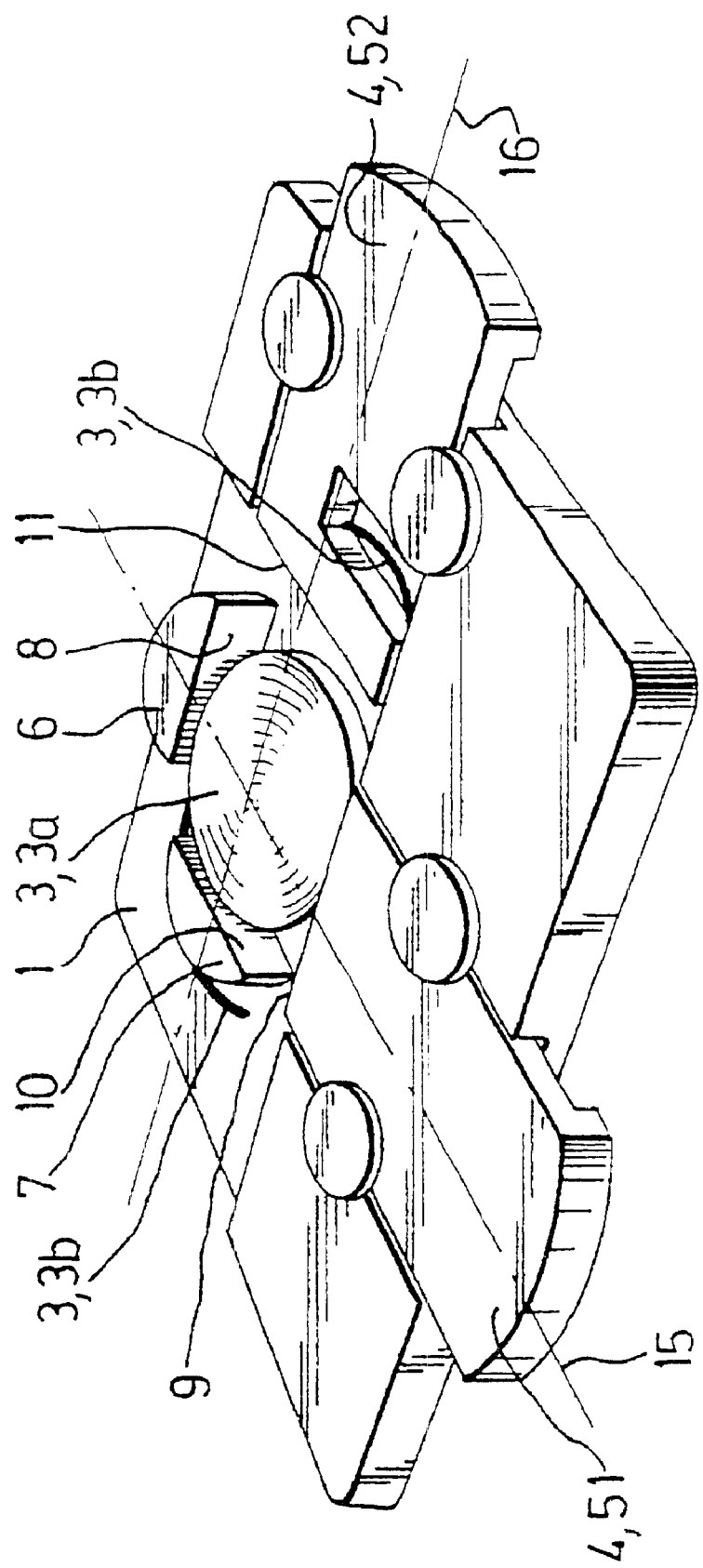

The embodiment in FIG. 8 differs from the previous one in that the mobile manoeuvring unit 42 is replaced by two mobile manoeuvring units 51, 52, which are guided in translation on the frame 1, one for each pair of bending support surfaces. In addition, in this embodiment, the device comprises a first pair of bending support surfaces 8, 9, which consist of a fixed bending support surface 8, which is integral with the frame 1, and a mobile bending support surface 9, which is formed from the end surface of the first mobile manoeuvring unit 51. Similarly, the second pair consists of a fixed bending support surface 10 which is integral with the frame 1, and a mobile bending support surface 11 which is formed from the end surface of the second mobile manoeuvring unit 52.

Each mobile manoeuvring unit 51, 52 is guided in translation relative to the frame 1, in a direction which corresponds to the diametral direction 15, 16, according to which the mobile bending support surface 9, 11 which it supports must be displaced. In this embodiment, the diametral directions 15, 16, and thus the corresponding bending lines, are at 90° relative to one another.

Figure 9:
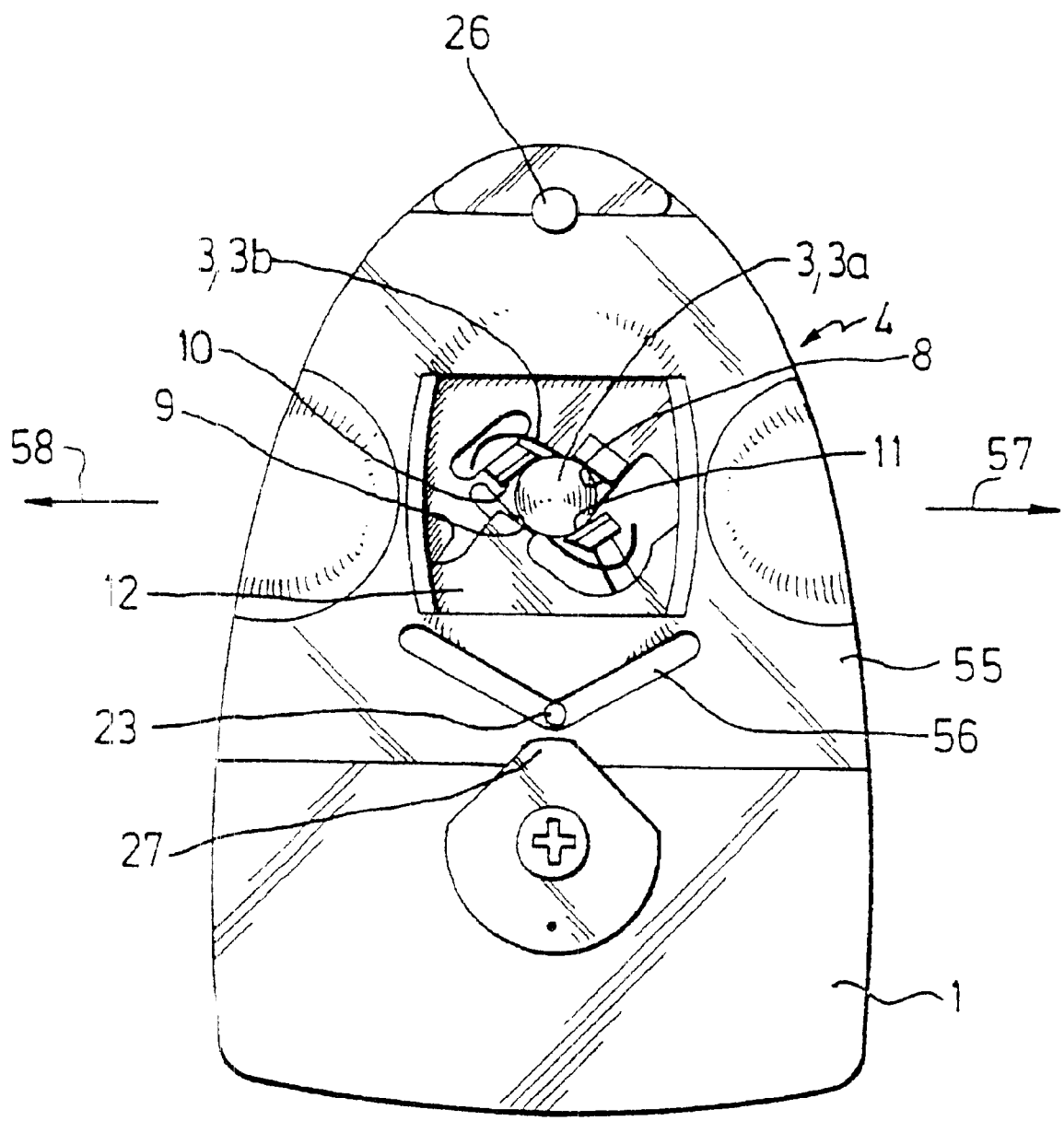
FIG. 9 is schematic plan view illustrating another embodiment of a device according to the invention.

The embodiment in FIG. 9 differs from that in FIGS. 3 and 4 in that the rotary mobile manoeuvring unit 18 is replaced by a mobile manoeuvring unit 55, which is guided in translation according to a single direction (i.e. according to a single axis of translation), in one direction or the other, relative to the frame 1.

The slide 23 of the intermediate mobile part 12 is engaged in a cam 56 in the shape of a "V" of the mobile manoeuvring unit 55, the branches of this cam 56 being designed such that the first direction of translation 57 of the unit 55 corresponds to the first method for actuation, i.e. to the displacement of the mobile bending support surface 9 of the first pair, for 6 o'clock-12 o'clock bending of the lens 3, and such that the second direction of translation 58, opposite the first, corresponds to the second method for actuation, i.e. to the displacement of the mobile bending support surface 11 of the second pair, for 3 o'clock-9 o'clock bending of the lens.

Figure 10:
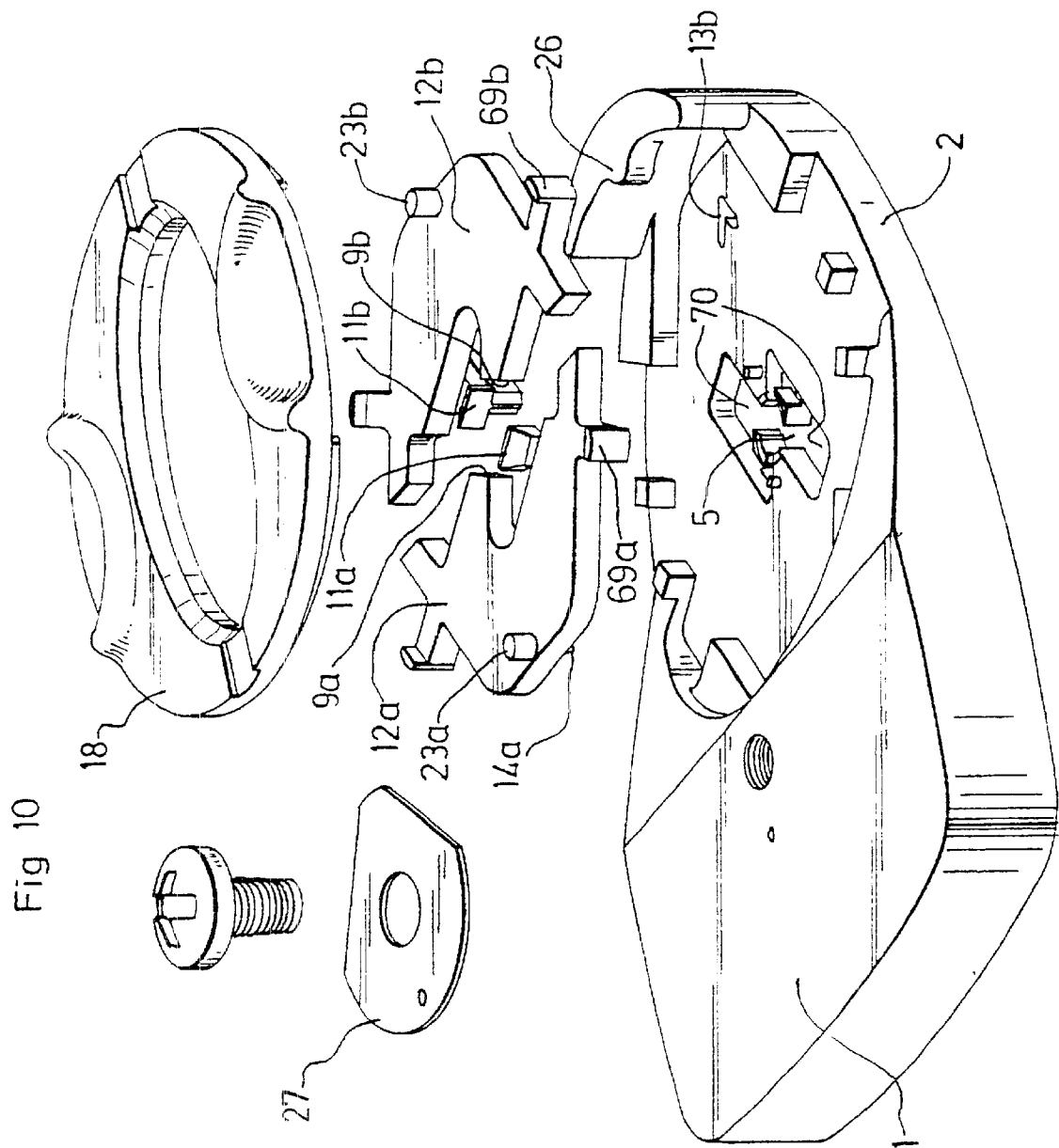
FIGS. 10 and 11 are exploded schematic perspective views respectively from three-quarters above, and three-quarters below, of another embodiment of a device according to the invention.
Figure 11:
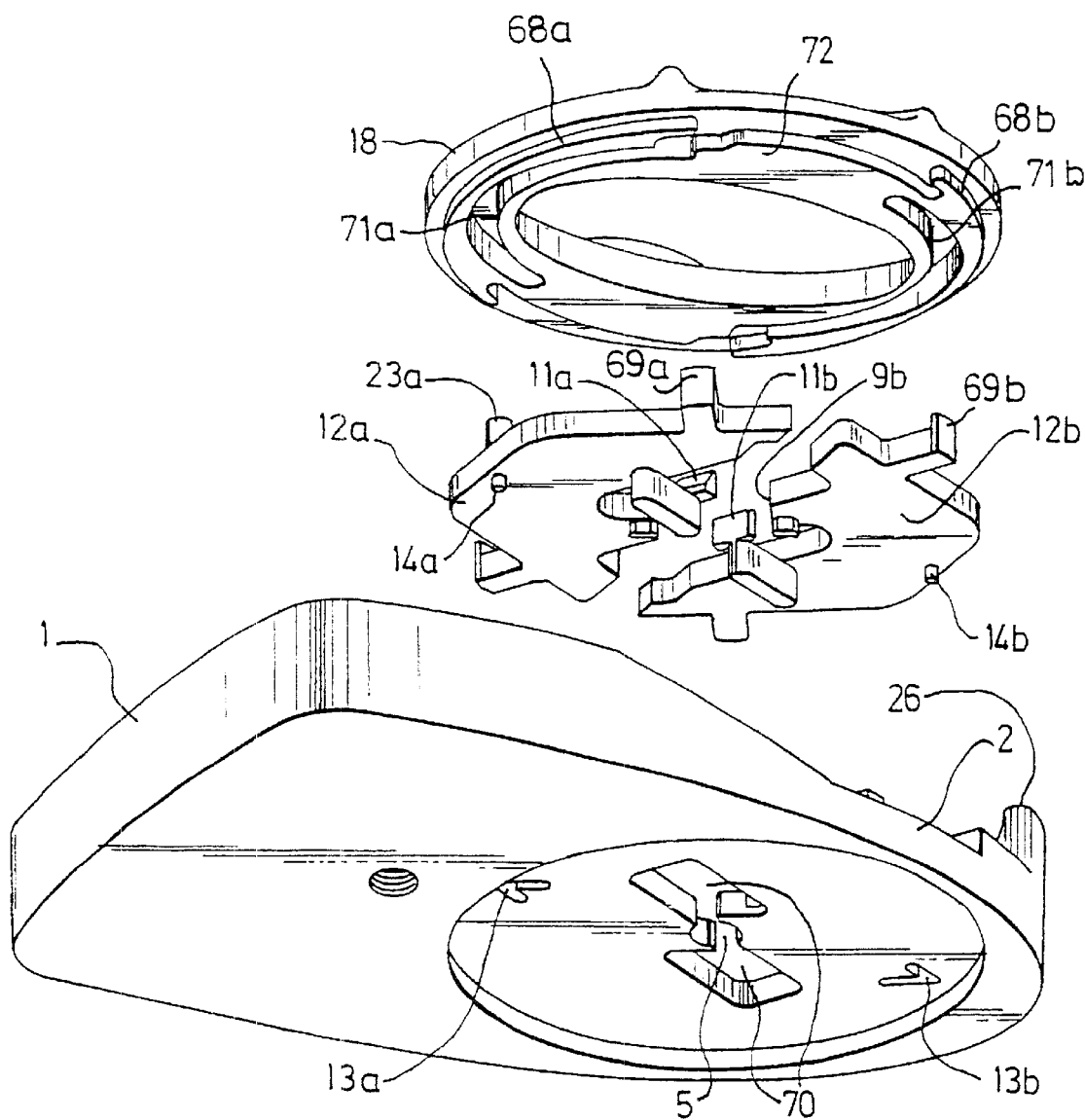

The embodiment in FIGS. 10 and 11 is similar to that in FIGS. 3 and 4, but comprises two intermediate mobile parts 12a, 12b, which define two pairs of mobile bending support surfaces 9a, 9b, 11a, 11b. Each intermediate mobile part 12a, 12b is guided in translation on the frame 1, by means of at least one groove 13a, 13b in the shape of a "V" in the base 2 of the frame 1, which receives at least one lug 14a, 14b, which is integral respectively with the corresponding intermediate mobile part 12a, 12b. In the embodiment shown, a single groove 13a 13b in the shape of a "V" is provided for each mobile part 12a, 12b, which is also guided by circular guide support surfaces 68a, 68b of the mobile manoeuvring unit 18, which receives pins 69a, 69b of the part 12a, 12b. The mobile manoeuvring unit 18 is also similar to that of the embodiment in FIGS. 3 and 4, it is in the shape of a ring, and is guided in rotation relative to the frame 1. However, this mobile manoeuvring unit 18 comprises two cams 71a, 71b provided recessed in its lower surface 72, in order to receive respectively a contact slide 23a, 23b, which projects towards the top of each intermediate mobile part 12a, 12b.

Each pair of mobile bending support surfaces 9a, 9b and 11a, 11b comprises a first support surface 9a, 11a, which is integral with the first intermediate mobile part 12a, and a second support surface 9b, 11b, which is integral with the second intermediate mobile part 12b.

The shape of the cams 71a, 71b of the mobile manoeuvring unit 18 and of the means 13a, 14a, 13b, 14b for guiding the intermediate mobile parts 12a, 12b relative to the frame 1, is designed such that, when the mobile manoeuvring unit 18 is displaced in a first direction of rotation, the two intermediate mobile parts 12a, 12b are displaced in translation such as to draw closer towards one another in the same first diametral direction, the mobile bending support surfaces 9a, 9b of a first pair drawing closer to one another, the lugs 14a, 14b being guided in the first branches, which are parallel to one another, of the grooves 13a, 13b, and, when the mobile manoeuvring unit 18 is displaced in the second direction of rotation, opposite the first, the intermediate mobile parts 12a, 12b are displaced in translation, and draw closer to one another in the same diametral direction, which is different from the first, the mobile bending support surfaces 11a, 11b of a second pair drawing closer to one another, and the lugs 14a, 14b being guided in the second branches, which are parallel to one another, of the grooves 13a, 13b.

The mobile manoeuvring unit 18 caps the two intermediate mobile parts 12a, 12b, and is kept in place axially relative to the frame 1, by means of the stops 26, 27.

In addition, according to this embodiment, the base 2 comprises a central recess 5 for reception of the lens to be bent, and receptacles 70 for accommodation of the haptic loops.

The embodiment in FIGS. 10 and 11 is thus similar to that in FIGS. 3 and 4, and differs from the latter substantially only in that the fixed bending support surfaces 8, 10 in FIGS. 3 and 4 are replaced by mobile bending support surfaces 9b, 11b, which are integral with a second intermediate mobile part 12b.

In the embodiment in FIGS. 10 and 11, the device substantially consists of four parts which are mobile relative to one another, i.e. the frame 1, the two intermediate mobile parts 12a, 12b, and the mobile manoeuvring unit 18.

The invention can form the basis of other variant embodiments. In addition, certain characteristics of the different variants can be combined with one another.

The invention can also be applied to bending of intraocular lenses with haptic parts which are not loops in the shape of a "C".

In addition, it is also possible to provide more than two different bending lines, for a single case for bending, according to the invention.

What is claimed is:

1. A device for bending an intraocular lens (3) with a flexible optical part (3a), before the lens is implanted, comprising:

a base (2) for reception of a lens (3) to be bent;

at least one pair of bending support surfaces (8,9,9a,9b, 10,11,11a,11b) placed to come in contact with an optical part (3a) of the lens (3) in two areas of contact which are opposite according to a single diametral direction;

a maneuvering element connected to one bending support surface of the at least one pair of bending support surfaces, and actuatable to control displacement towards another bending support surface (8,9b,11b, 11a) of the at least one pair of bending support surfaces, wherein the maneuvering element is designed such that, with a lens (3) in place in the base according to a first actuation of the maneuvering element, a first pair of bending support surfaces (8,9,9a,9b) comes into contact with a periphery of the optical part (3a) of the lens (3), in two areas of contact which are opposite according to a first diametral direction (15), this first pair of bending support surfaces (8,9,9a,9b) being designed, under the effect of actuation of at least one mobile maneuvering unit (18,42,51,52,55,62a,62b) to produce bending of the lens according to a first bending line;

according to a second actuation of the maneuvering element, a second pair of bending support surfaces (10,11,11a,11b), which is distinct from the first pair of bending support surfaces, comes into contact with the periphery of the optical part (3a) of the lens (3), in two areas of contact which are opposite according to a second diametral direction (16), which is different from the first diametral direction (15), this second pair of bending support surfaces (10,11,11a, 11b) being designed, under the effect of actuation of the at least one mobile maneuvering unit (18,42,51, 52,55,62a,62b) to produce bending of the lens according to a second bending line, which is distinct from the first bending line, such that the lens (3) can be bent according to one or the other of the different bending lines.

2. A device as claimed in claim 1, wherein the first diametral direction (15) and the second diametral direction (16) form between one another an angle of between 60° and 120°, such that the lens (3) can be bent according to one or the other of two bending lines which form between one another an angle of between 60° and 120°.

3. A device as claimed in claim 1, further comprising a frame (1) which includes the base, at least one of a pair of bending support surfaces wherein at least another of the pair of bending support surfaces is fitted relative to the frame (1) to be drawn closer to the one bending support surface of this pair of bending support surfaces, and the maneuvering element comprises at least one mobile maneuvering unit connected to at least the one bending support surface, in order to control the displacements of the one bending relative to the base, when this mobile maneuvering unit is actuated.

4. A device as claimed in claim 1, wherein the maneuvering element comprises at least two mobile maneuvering units (51, 52), one unit connected to at least one first mobile bending support surface (9) of a first pair of bending support surfaces (8,9), and the other unit (52) connected to at least one second mobile bending support surface (11) of a second pair of bending support surfaces (10,11).

5. A device as claimed in claim 1, wherein the maneuvering element comprises a mobile maneuvering unit (18, 42,55) connected to at least one first mobile bending support surface (9,9a,9b) of the first pair of bending support surfaces (8,9,9a,9b), and to at least one second mobile bending support surface (11,11a,11b) of the second pair of bending support surfaces (10,11,11a,11b), and is actuatable according to both the first actuation and according to the second actuation.

6. A device as claimed in claim 5, wherein the mobile maneuvering unit (18) is fitted to rotate relative to the frame (1), the first actuation corresponds to displacement in rotation of the mobile maneuvering unit (18) in a first direction of rotation (24), and the second actuation corresponds to displacement in rotation of the mobile maneuvering unit (18) in the second direction of rotation (25), opposite to the first direction of rotation (24).

7. A device as claimed in claim 5, wherein the mobile maneuvering unit (42) is fitted relative to the frame (1) and can be displaced according to at least two distinct directions (49,50) of translation, one direction (49) corresponding to the first actuation (50) and a second direction corresponding to the second actuation.

8. A device as claimed in claim 5, wherein the mobile maneuvering unit (55) is fitted relative to the frame (1) to be displaced according to at least one direction of translation, and according to at least two opposite directions (57,58) according to this direction of translation corresponding to the first actuation and to the second actuation.

9. A device as claimed in claim 5, wherein a first mobile bending support surface (9) of the first pair of bending support surfaces (8,9) and a second mobile bending support surface (11) of the second pair of bending support surfaces (10,11) are integral with a single intermediate mobile part (12), the mobile part being fitted and guided relative to the frame (1), and is connected to the mobile maneuvering unit (18) to be entrained in displacement under the effect of actuation of this mobile maneuvering unit (18).

10. A device as claimed in claim 1, wherein a mobile maneuvering unit (18,42,55) is connected to, and controls displacement of, each mobile bending support surface (9,9a, 9b,11,11a,11b) by a cam and contact slide system.

11. A device as claimed in claim 1, wherein each pair of bending support surfaces comprises a bending support surface (8, 10) fixed relative to a frame (1).

12. A device as claimed in claim 1, wherein each mobile bending support surface is fitted relative to a frame, to be mobile at least substantially in translation.

13. A device as claimed in claim 1, wherein the base is designed to receive the intraocular lens oriented according to a single possible direction only.

14. A device as claimed in claim 1, further comprising packaging for an intraocular lens (3), and wherein the base comprises a cap (30) closed onto the lens (3), this cap (30) being openable to permit access to the lens (3).

15. A device as claimed in claim 14, wherein the cap (30), in the position in which it is closed onto the lens (3), prevents any premature displacement of the maneuvering element, and, in an open position, permits actuation of the maneuvering element.

16. An intraocular lens bending device, comprising:
a frame;
a base within the frame, the base shaped for receiving an intraocular lens to be bent, the lens comprising an optical part made of a flexible material and two C-shaped haptic loops;
a maneuvering element fitted onto the frame, the maneuvering element being operable for bending the lens;
a cylindrical recess provided in the base, the recess being positioned to be opposite the optical part of the lens and having a diameter smaller than the optical part of the lens;
two fixed studs supported by the base, the two studs being disposed substantially at 90 degrees relative to one another, adjacent the central recess;
a surface on each stud extending upwards from the base substantially perpendicularly to a radial direction of the central recess and defining a fixed bending support surface, the fixed bending support surfaces positioned to come into contact with a periphery of the optical part of the lens;
three grooves located on a surface of the base;
a bendable intermediate mobile part fitted on the frame, and guided by the grooves, the intermediate mobile part having three lugs, each lug engaged in one of the grooves;
each of the grooves comprising a first branch and a second branch, the grooves being parallel to one another;
an angle formed between the first branch and the second branch of the grooves, the angle defining two potential bending lens for the lens, the intermediate mobile part being displaceable in translation relative to the base in directions corresponding to directions of the first and second branches of the groove; and
two pairs of bending support surfaces positioned to come into contact with the periphery of the optical part of the lens,
the first pair of the two pairs of bending support surfaces comprising a fixed bending support surface integral with the base and a mobile support surface integral with the intermediate mobile part,
the second pair of the two pairs of bending support surfaces comprising a fixed bending support surface integral with the base and a mobile support surface integral with the intermediate mobile part.

17. The device of claim 16, wherein the frame is shaped to be grasped in a first hand of a user and be by a second hand of the user to operate the maneuvering element.

18. The device of claim 16, further comprising:
a ring-shape rotary mobile maneuvering unit having a recessed central part providing an access opening opposite the lens when in place on the base,
a cylindrical guide surface extending upward from the base; and
a circular outer edge of the mobile maneuvering unit slidingly contacting the cylindrical guide surface,
the maneuvering element being positioned between the mobile maneuvering unit and the base,
the maneuvering element being guided by the rotary maneuvering unit with respect to the base.

19. An intraocular lens bending device, comprising:
a frame;
a base within the frame, the base shaped for receiving an intraocular lens having an optical part and two C-shaped haptic loops;
a maneuvering element fitted onto the frame, the maneuvering element being operable for bending the lens;
a cylindrical recess provided in the base, the recess being positioned to be opposite the optical part of the lens;
two fixed studs supported by the base, the two studs being disposed substantially at 90 degrees relative to one another, adjacent the central recess;
a surface on each stud extending upwards from the base substantially perpendicularly to a radial direction of the central recess and defining a fixed bending support surface, the fixed bending support surface positioned to come into contact with a periphery of the optical part of the lens;
three V-shaped grooves located on a surface of the base, each of the grooves comprising a first branch and a second branch,
the grooves being parallel to one another,
an angle formed between the first branch and the second branch of the grooves, the angle defining two potential bending lens for the lens;
a bendable intermediate mobile part fitted on the frame and guided by the grooves, the intermediate mobile part having three lugs, each lug engaged in one of the grooves;

the intermediate mobile part being displaceable in translation relative to the base in directions corresponding to directions of the first and second branches of the groove; and two pairs of bending support surfaces positioned to come into contact with the periphery of the optical part of the lens, the first pair of the two pairs of bending support surfaces comprising a fixed bending support surface integral with the base and a mobile support surface integral with the intermediate mobile part, the second pair of the two pairs of bending support surfaces comprising a fixed bending support surface integral with the base and a mobile support surface integral with the intermediate mobile part.

* * * * *